United States Patent [19]

Rideout et al.

[11] Patent Number: 5,086,044
[45] Date of Patent: * Feb. 4, 1992

[54] TREATMENT OF HUMAN VIRAL INFECTIONS

[75] Inventors: Janet L. Rideout, Raleigh; David W. Barry, Chapel Hill; Sandra N. Lehrman, Durham; Martha H. St. Clair, Durham; Phillip A. Furman, Durham, all of N.C.

[73] Assignee: Burroughs Wellcome Co., Research Triangle Park, N.C.

[*] Notice: The portion of the term of this patent subsequent to Feb. 9, 2005 has been disclaimed.

[21] Appl. No.: 510,590

[22] Filed: Apr. 18, 1990

Related U.S. Application Data

[60] Division of Ser. No. 140,967, Jan. 6, 1988, abandoned, which is a continuation of Ser. No. 877,796, Jun. 23, 1986, abandoned.

[51] Int. Cl.$^5$ .............................................. A61K 31/70
[52] U.S. Cl. ...................................... 514/51; 514/934
[58] Field of Search ............................. 514/50, 51, 943

[56] References Cited

U.S. PATENT DOCUMENTS 4,724,232  2/1988  Rideout et al. ........................ 514/50

OTHER PUBLICATIONS

Hartshorn et al., Antimicrobial Agents of Chemotherapy, vol. 31, No. 2, Feb., 1987, Synergistic Inhibition of Human Immunodeficiency Virus In Vitro by Azidothymidine and Recombinant Alpha A Interferon, pp. 168–172.
Lane et al., The Lancet, Nov. 26, 1988, Anti-Retroviral Effects of Interferon-αIn Aids-Associated Kaposi's Sarcoma, pp. 1218–1222.
DeWit et al., The Lancet, Nov. 26, 1988, Clinical and Virological Effects of High-Dose Recombinant Interferon-αIn Disseminated Aids-Related Kaposi's Sarcoma, pp. 1214–1217.
Paper—J. Interferon Res. 7(6):774, 1987.
J. M. Yeo, Journal of Infec., 1989, 18, Supplement 1, pp. 93–96, Current and future trials with zidovudine.
Ho et al., The Lancet, Mar. 16, 1985, Recombinant Human Interferon Alfa-A Suppresses HTLV-III Replication in Vitro, pp. 602–604.
Zidovudine/Interferon Combination Therapy, Apr. 17, 1988, 17 pages.
Orholm et al., Current Science Ltd., vol. 3, No. 2, Suppression of p. 24 Antigen in Sera from HIV-Infected individuals with low-doseα-interferon and zidovudine: a pilot study, pp. 97–100.
Paper—The Lancet, Jan. 21, 1989, Interferon-Alpha Plus Zidovudine in HIV Infection, page 156.
Paper—Carron et al., No. 3633, Anti-HIV Activity of Beta-Interferon in Combination with Zidovudine.
Paper—vol. 260, No. 23, Dec. 16, 1988, From the National Institutes of Health, Progress in Aids Research, p. 3406.
Dozier et al., Drug. Intell. Clin. Pharm., 17(11), pp. 798–807, Nov., 1983, Acquired Immune Deficiency Syndrome and the Management of Associated Opportunistic Infections.
Paper—The Lancet, Jan. 30, 1988, Combination Therapy After Retroviral Inoculation, pp. 239–240.
Daul et al., Annals of Allergy, vol. 51, Sep. 1983, Acquired Immune Deficiency Syndrome: An Update and Interpretation, pp. 351–361.
Paper—C-21, Aids, Proceedings of Asco, vol. 4, Mar. 1985.

Primary Examiner—John W. Rollins
Attorney, Agent, or Firm—Donald Brown; Lawrence A. Nielsen

[57] ABSTRACT

Treatment of AIDS or humans carrying or infected with the AIDS virus or having antibodies to the AIDS virus is disclosed using the compound 3'-azido-3'-deoxythymidine or a pharmaceutically acceptable basic salt thereof. Also disclosed is the use of the 5'-mono-, di- and triphosphate of 3'-azido-3'-deoxythymidine or a pharmaceutically acceptable basic salt thereof for the same purpose. Additionally, there is disclosed the treatment of Kaposi's sarcoma with 3'-azido-3'-deoxythymidine (AZT) and the synergistic activity in the treatment of humans infected with HTLV-III of AZT and interferon as well as AZT and acyclovir.

3 Claims, No Drawings

TREATMENT OF HUMAN VIRAL INFECTIONS

This is a divisional of copending application Ser. No. 07/140,967 filed on 1/6/88, now abandoned, which is a continuation of Ser. No. 06/877,796 filed 06/23/86, now abandoned.

The acquired immunodeficiency syndrome (AIDS) is considered to be caused by the HIV III virus (also identified as HTLV III/LAV). HTLV III is an RNA genetically unique retrovirus, having a gene not found to date in other retroviruses, which allows it to rapidly replicate in a human host cell. The HTLV III virus appears to preferentially attack helper T-cells (T-lymphocytes or OK4-bearing T-cells as they are sometimes known) and possibly other human cells, e.g., certain cells within the brain. The helper T-cells are invaded by the virus and the T-cell becomes an HTLV III virus producer. The helper T-cells are quickly destroyed and their number in the human being is depleted to such an extent that the body's B-cells as well as other T-cells normally stimulated by helper T-cells no longer function normally or produce sufficient lymphokines and antibodies to destroy the invading virus or other invading microbes, etc.

While the HTLV III virus does not necessarily cause death per se, it does in many cases cause the human's immune system to be so severely depressed that the human falls prey to various other diseases (secondary infections or unusual tumors) such as herpes, cytomegalovirus, Kaposi's sarcoma and Epstein-Barr virus related lymphomas among others. These secondary infections are separately treated using other medications as is conventional. In some humans infected with HTLV III virus, (hereinafter referred to the AIDS virus and which is meant herein to include mutants thereof) humans seem to live on with little or no symptoms, but appear to have persistent infections. Another group of humans suffers mild immune system depression with various symptoms such as weight loss, malaise, fever, swollen lymph nodes. These syndromes have been called persistent generalized lymphadenopathy syndrome (PGL) and AIDS related complex (ARC) and may or may not develop into AIDS.

In all cases, those infected with the AIDS virus (HTLV III virus) are believed to be persistently infective to others.

It has now been discovered that the compound known as 3'-azido-3'-deoxthymidime having the formula I

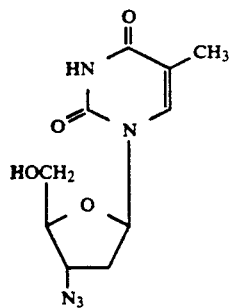

(I)

is useful in treating humans identified as having AIDS as well as humans identified as infected by or carrying the AIDS virus or having antibodies to the AIDS virus in order to inhibit the acquired immunodeficiency syndrome from developing in such humans or being transmitted to others. Tests with the compound of formula I in humans has shown that the amount of AIDS virus is significantly reduced at least transiently, the number of helper T-cells, T-cells and platelets are increased over those before treatment and in two cases to date the immune system appears to have been reestablished (restored) in so far as the human patient's ability to amount a delayed hypersensitivity skin test immune response was restored.

The compound of formula I may be administered per se or in the form of a pharmaceutically acceptable salt, e.g., an alkali metal salt such as sodium or potassium, an alkaline earth salt or an ammonium salt (all of which are hereinafter referred to as a pharmaceutically acceptable base salt).

The salts of the compound convert to the compound per se after being administered to the human and are thus prodrugs. The compound 3'-azido-3'-deoxythymidine penetrates into the infected cells after contacting same and is converted by the enzymes of cells such as T lymphocytes, astroglia cells, macrophages and others to the monophosphate thereof. The monophosphate is then converted by the cellular enzymes to the diphosphate of the compound of formula I and ultimately to the triphosphate of the compound of formula I.

In human cells infected with the human aids virus the mono- and triphosphate of the compound of formula I act as inhibitors of the viral reverse transcriptase necessary for viral replication. All prodrugs (precursors) are administered to a human in an amount sufficient to generate an effective amount of the compound which contacts the AIDS virus and interacts with it (e.g., prevents replication thereof).

Thus the compound of formula I can be said to be a pro-drug after entering the human T-lymphocytes or other human cells since it is an intermediate (precursor) to the mono-, di- and triphosphate thereof.

It is believed that the mono-, di- and triphosphates of the compound of formula (I) can also be said to be prodrugs since they would invariably (at least in part) by hydrolized in the body to 3'-azido-3'-deoxythymidine which is taken up by the cells.

As another feature of this invention, there is also disclosed the method of administering to a human in need thereof the mono-, di-, or triphosphate of the compound of formula I or their pharmaceutically acceptable base salts (i.e., alkali metal, alkaline earth or ammonium salt) to treat AIDS, to inhibit the replication of the AIDS virus in infected human cells and to prevent AIDS from developing in humans infected with the AIDS virus or carrying antibodies to the AIDS virus. The mono-, di- and triphosphates of 3'-azido-3'-deoxythymidine are of the formulas II, III and IV respectively.

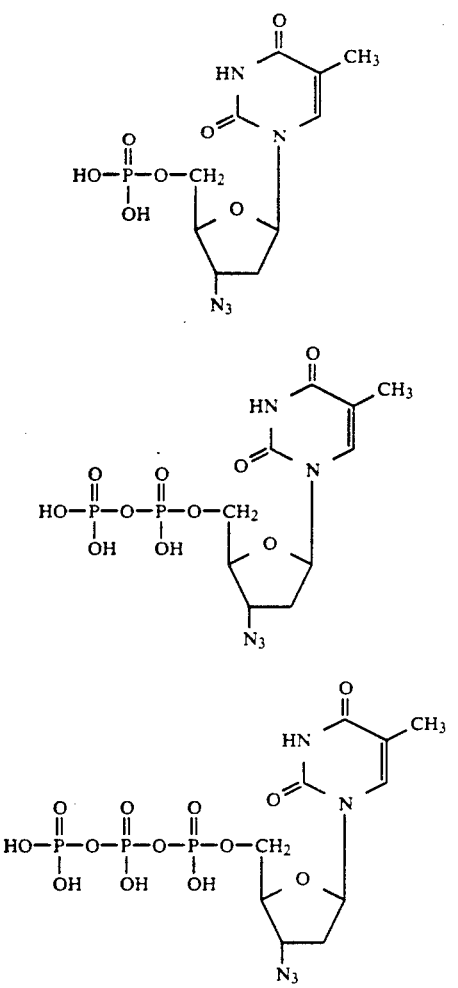

The present invention also discloses compounds of formulas I, II, III and IV and their appropriate salts for use in the treatment of the conditions referred to above, as well as the use of such compounds in the preparation of pharmaceutical formulations for the treatment of such conditions. The above mentioned pharmaceutically acceptable salts may be prepared in a conventional manner, e.g., treatment of the compound with an appropriate base.

In general for the above AIDS virus infections, a suitable effective dose of the 3'-azido-3'-deoxythymidine compound, its pharmaceutically acceptable basic salts, its mono-, di- or triphosphates or their pharmaceutically acceptable basic salts (all of which are herein after referred to as the administered ingredient) will be in the range 5 to 250 mg per kilogram body weight of recipient per day, preferably in the range of 7.5 to 100 mg per kilogram body weight per day and most preferably in the range 10 to 40 mg per kilogram body weight per day. In a clinical program in treating humans with AIDS, the compound 3'-azido-3'-deoxythymidine is being administered as an infusion (IV) at 1 and 2.5 mg/kilogram every eight hours. The desired dose is preferably presented as two, three, four or more sub-doses administered at appropriate intervals throughout the day. These sub-doses may be administered as unit dosage forms, for example, containing 5 to 500 mg, preferably 10 to 200 mg and most preferably 20 to 100 mg of active ingredient per unit dosage form.

Administration may be by any suitable route including oral, rectal, nasal, topical (including buccal and sublingual), vaginal and parenteral (including subcutaneous, intramuscular, intravenous and intradermal) with oral or parenteral being preferred. It will be appreciated that the preferred route may vary with, for example, the condition and age of the recipient.

A preferred dose is administered to achieve peak plasma concentrations of the compound of formula I, its mono-, di- or triphosphate or its pharmaceutically acceptable salts of from about 1 to about 100 $\mu$M, preferably about 5 to 80 M, most preferably about 7.5 to about 50 $\mu$M. This may be achieved, for example, by the intravenous injection of a sterile 0.1 to 5% solution of the administered ingredients in saline as a bolus containing about 1 to about 80 mg/kg of the active ingredient. Desirable blood levels may be maintained by a continuous infusion to provide about 0.01 to about 0.8 mg/kg/hour or by intermittent infusions providing about 0.04 to about 20 mg/kg of the administered ingredient.

The administered ingredients may be used in therapy in conjunction with other medicaments such as 9-[[2-hydroxy-1-(hydroxymethyl)ethoxy]methyl]guanine, 9-(2-hydroxyethoxymethyl)guanine (acyclovir), 2-amino-9-(2-hydroxyethoxymethyl)purine, suramin, ribavirin, antimoniotungstate (HPA-23), interferon, e.g., $\alpha$ interferon, interleukin II, and phosphonoformate (Foscarnet) or in conjunction with other immune modulation including bone marrow or lymphocyte transplants or other medications such as levamisol or thymosin which would increase lymphocyte numbers and/or function as is appropriate.

The compound of formula I, 3'-azido-3'-deoxythymidine, (sometimes also referred as zidothymidine) is disclosed in J. R. Horwitz et al. *J. Org. Chem.* July 29, 1964; also see *Biochemical Pharmacology*, Vol. 29, pp. 1849-1851; C. J. Kreig et al, *Experimental Cell Research* 116 (1978) pp. 21-29. Also see W. Ostertag et al, *Proc. Nat. Acad. Sci. U.S.A.* 71 (1974) for some of its biological activities.

While it is possible for the administered ingredients to be administered alone, it is preferably to present them as part of a pharmaceutical formulation. The formulations of the present invention comprise at least one administered ingredient, as above defined, together with one or more acceptable carriers thereof and optionally other therapeutic ingredients. The carrier(s) must be "acceptable" in the sense of being compatible with the other ingredients of the formulation and not deleterious to the recipient thereof.

The formulations include those suitable for oral, rectal, nasal, topical (including buccal and sublingual), vaginal or parenteral (including subcutaneous, intramuscular, intravenous and intradermal) administration. The formulations may conveniently be presented in unit dosage form, e.g., tablets and sustained release capsules, and may be prepared by any methods well known in the art of pharmacy.

Such methods include the step of bringing into association the to be administered ingredients with the carrier which consitutes one or more accessory ingredients. In general, the formulations are prepared by uniformly and intimately bringing into association the active ingredient with liquid carriers or finely divided solid carriers or both, and then if necessary shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion and as a bolus, etc.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, suface-active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein.

Formulations suitable for topical administration in the include lozenges comprising the ingredients in a flavoured basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin may be presented as ointments, creams, gels and pastes comprising the ingredient to be administered and a pharmaceutically acceptable carrier. A preferred topical delivery system is a transdermal patch containing the ingredient to be administered.

Formulations for rectal administration may be presented as a suppository with a suitable base comprising, for example, cocoa butter or a salicylate.

Formulations suitable for nasal administration wherein the carrier is a solid include a coarse powder having a particle size, for example, in the range 20 to 500 microns which is administered in the manner in which snuff is taken, i.e., by rapid inhalation through the nasal passage from a container of the powder held close up to the nose. Suitable formulations wherein the carrier is a liquid, for administration, as for example, a nasal spray or as nasal drops, include aqueous or oily solutions of the active ingredient.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a frre-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above recited, or an appropriate fraction thereof, of the administered ingredient.

It should be understood that in addition to the ingredients particularly mentioned above the formulations of this invention may include other agents conventional in the art having regard to the type of formulation in question, for example, those suitable for oral administration may include flavouring agents.

The LD50 for 3'-azido-3'-deoxythimidine in mice and rats was found to be greater than 750 mg/kg.

The following examples illustrate the invention.

EXAMPLE 1

Preparation of 2,3'-Anhydrothymidine

Thymidine (85.4 g; 0.353 mol) was dissolved in 500 mL dry DMF (dimethyl formamide) and added to N-(2-chloro-1,1,2-trifluoroethyl)diethylamine (100.3 g; 0.529 mol) [prepared according to the method of D. E. Ayer, *J. Med. Chem.* 6, 608 (1963)]. This solution was heated at 70° C. for 30 minutes then poured into 950 mL ethanol with vigorous stirring. The product precipitated from this solution and was filtered. The ethanol supernatant was refrigerated then filtered to yield a total of 47.75 g (0.213 mol; 60.3%) of 2,3'-anhydrothymidine mp=228°-230° C.

EXAMPLE 2

Preparation for 3'-Azido-3'-doexythymidine 2,3'-Anhydrothymidine (25 g; 0.1115 mol) and NaN$_3$ (29 g; 0.446 mol) was suspended in a mixture of 250 mL DMF and 38 mL H$_2$O. The reaction was refluxed for 5 hours at which time it was poured into 1 liter of H$_2$O. This aqueous solution was extracted with ethyl acetate (EtOAc) (3×700 ml). The EtOAc was dried over Na$_2$SO$_4$, filtered, and then EtOAc was removed in vacuo to yield a viscous oil. This oil was stirred with 200 mL water resulting in a solid, 3'-azido-3'-deoxythymidine, 9.15 g (0.0342 mol; 30.7%) mp=116°-118° C.

EXAMPLE 3

Preparation of Sodium Salt of 3'-deoxythymidine

Approximately one gram of 3'-azido-3'-deoxythymidine was dissolved in 50 mL of distilled water. The pH was adjusted to 12 with 1N NaOH. Approximately half of the solution was freeze dried. A white powder, the sodium salt of 3'-azido-3'-deoxthymidine on the 0.6 hydrate, 0.415 g, resulted.

Analysis calculated for $C_{10}H_{12}N_5NaO_4 \cdot 6/10 H_2O$. Calculated: C, 40.03; H, 4.43; N, 23.34; Na, 7.66. Found: C, 39.88; H, 4.34; N, 23.29; Na, 7.90.

EXAMPLE 4

Preparation of 5'-Monophosphate of 3'-Azido-3'-deoxythymidine

3'-Azido-3'-deoxythymidine (0.5 g, 1.87 mmol) was dissolved in 5 mL of triethyl phosphate and the mixture was cooled to −50° C. Phosporus oxychloride (0.685 mL, 7 mmol) was added in one portion to the rapidly stirred solution which was then maintained at −10° C. for 22 hours. An aliquot was removed and added to concentrated ammonium hydroxide. Analysis of this sample on TLC (cellulose, n-ProH:H$_2$O, 7:3 v/v) showed no remaining starting material and a single fluorescent spot with lower mobility than the nucleoside. The reaction mixture was poured into 20 mL of ice and water. This was placed in an ice bath and the pH of the solution was adjusted to a value of 7.5 by the addition of 2N NaOH. The basic mixture was extracted once with chloroform and one with ether. The aqueous layer was again adjusted to give a pH of 7.5 and concentrated in vacuo to remove residual organic solvent. The material was stored at −100° C. until purified as follows:

Deactivated charcoal was prepared by washing coconut charcoal (50-200 mesh, 100 g) with 500 mL of 1N HCl, 3 L of water, 35 mL of 3% toluene in 95% ethanol, 600 mL of 95% ethanol and finally extensively with water. Deactivated charcoal (12 mL of settled wet charcoal) was added with stirring to the monophosphate solution (0.72 g, 1.8 mmol, 30 mL). The supernatant was decanted and the charcoal was washed with 150 mL of water. The nucleotide was eluted from the charcoal by washing with 120 mL of 1.5M ammonium hydroxide in 50% ethanol. This solution was filtered through a 0.22 micron filter, concentrated in vacuo to 10 mL, filtered through a Amicon Centrilo CF-25 membrane, and lyophilized. The yield of diammonium 3'-azido-3'-doexythymidine-5'-monophosphate was 0.36 g (0.94 mmol, 52%). This compound was characterized as a nucleoside 5'-monophosphate by the ability of 5'-nucleotidase to degrade it to the nucleoside.

EXAMPLE 5

Preparation of the 5'-Di- and Triphosphate of 3'-Azido-3'-doexythymidine

The di- and triphosphate of 3'-azido-3'-doexythymidine were prepared from the ammonium salt of the 5'-monophosphate of 3'-aizdo-3'-deoxythymidine by a four step sequence.

Step I

Preparation of Bis(Tri-n-butylammonium) Pyrophosphate

A column of DOW 50 pyridinium resin was prepared by pouring 40 mL of resin into a 25 cm diameter column and washing with water until no more color eluted. Sodium pyrophosphate decahydrate (1.12 g, 2.51 mmol) was dissolved in 30 mL of water and applied to the column. The column was eluted with water. A 125 mL fraction of the eluant which contained UV absorbing material was collected. The volume was reduced to 10 mL in vacuo and tri-n-butylamine (1.2 mL) was added. The volume was reduced in vacuo and the residue was dried by coevaporation with pyridine four times. The product was stored in a freezer (−5° C.).

Step II

Preparation of the Acid Form of the Monophosphate of 3'-Azido-3-deoxythymidine

The acid form of the monophosphate was prepared by passing the ammonium salt (0.1 g, 0.283 mmol) dissolved in 6 mL of water, through a 1.5 mL (10 eq.) column of DOW 50 H+.

Step III

Preparation of Phosphoromorpholidate Derivative

The hydrogen form of the monophosphate, 0.283 mmol, was dissolved in 9 mL of water. Morpholine (99 μL, 1.13 mmol, 4 eq.) was added and the solution heated to reflux. Dicyclohexyl carbodiimide (0.234 g, 1.13 mmol, 4 eq.) dissolved in t-butanol (5 mL) was added over a three-hour period. The reaction was refluxed overnight. The reaction was cooled to room temperature, filtered, and the solvents removed in vacuo. Ethanol was added and evaporated in vacuo four times. The residue was dissolved in methanol and the phosphoromopholidate precipitated by the addition of ether. The precipitate was triturated with ether four times and dried on a rotary evaporator. A weight yield of 97 mG, 50%, was obtained.

Step IV

Preparation of the 5'-Di- and Triphosphates of 3'-Azido-3'-deoxythymidine

The phosphoromorpholidate derivative was dried by removal of pyridine in vacuo four times. The bis-(tri-n-butylammonium) pyrophosphate was also dried by removal of pyridine in vacuo. The phosphoromorpholidate was dissolved in pyridine, 5 mL, and added to the vessel containing the pyrophosphate reagent. The reaction was allowed to continue overnight at room temperature. The pyridine was removed in vacuo. Water was added to the residue and removed in vacuo three times. The residue was frozen.

The reaction mixture (0.09 g) was thawed and dissolved in 50 mL of water. The solution was applied to a column (1×10 cm) of DEAE Saphadex A-25 which had been equilibrated 50 mM ammonium bicarbonate. The phosphates were eluted with a 300 mL linear gradient of 50-800 mM ammonium bicarbonate. The fractions containing the diphosphate mucleotide were pooled as were those containing the triphosphate nucleotide. The pooled diphosphate and triphosphate fractions were each dried in vacuo, redissolved in water, dried again, redissolved in water and lyophilized. The yields were: the diphosphate as the triammonium salt, 0.014 g; the triphosphate, as the tetrammonium salt, 0.002 g.

EXAMPLE 6

Enzymatic Synthesis of the 5'-Triphosphate of 3'-Azido-3'-deoxythymidine

The 5'-triphosphate was synthesized from the 5'-diphosphate using pyruvate kinase and nucleoside diphosphate kinase. The reaction mixture contained: 6 mM 3'-azido TDP, 12 mM adenosine triphosphate, 40 mM MgCl 2, 40 mM potassium piperazine-N,N'-bis(2-ethanesulfonic acid) PIPES buffer, pH 6.8 ), 30 mM phosphenolpyruvate, 40 UI/ml nucleoside diphosphate kinase and 100 IU/ml pyruvate kinase in a final volume of 5 mL. The reaction mixture was incubated at 37° C. for 5 days. The reaction mixture was applied to a column (2.5×10 cm) of DEAE Saphadex A-25 which had been equilibrated with ammonium bicarbonate. The nucleotides were eluted with a gradient of 100–1000 mM ammonium bicarbonate. Fractions containing the triphosphate were pooled, and evaporated to dryness in vacuo. The compound was further purified using a preparative HPLC column (Whatman, Inc., Magnum 9 SAX) eluted with a gradient of 10–1000 mM potassium phosphate, ph 3.5. The resulting compound was further purified using a DEAE Saphadex A-25 column as above. The fractions containing the tetrammonium 3'-azido-3'-deoxythymidine-5'-triphosphate were pooled, dried in vacuo, redissolved in water and lyophilized to yield 0.008 g (0.01 mmol).

EXAMPLE 7

| Tablet Formulation | |
|---|---|
| 3'-Azido-3'-Deoxythymidine | 100 mg |
| Lactose | 200 mg |
| Starch | 50 mg |
| Polyvinylpyrrolidone | 5 mg |
| Magnesium stearte | 4 mg |
| | 359 mg |

Tablets were prepared from the foregoing ingredients by wet granulation followed by compression.

EXAMPLE 8

Capsule

A two part soft gelatin is prepared by placing the tablet formulation of Example 7 in a two part capsule.

EXAMPLE 9

| Sterile Injectable Formulation | |
|---|---|
| 3'-Azido-3'-deoxythymidine | 0.125 g |

The formulation is sterilized by heat and then placed in a sealed container, e.g., glass so that it may be administered by infusion or by injection.

EXAMPLE 10

The acid forms of the 5'-mono, di- and triphosphate nucleotides of 3'-azido-3'-deoxythymidine are prepared by passing the corresponding ammonium salts through DOW 50 H+ columns and lyphilizing the solutions obtained thereby.

It has also been discovered that 3'-azido-3'-deoxythymidine, its 5'-mono-, 5'-di-, and 5'-triphosphates and pharmaceutically acceptable salts thereof are useful in treating Kaposi's sarcoma in human beings, and this is another feature of this invention. The suitable effective dose range for this indication is the same as that used in the treatment of human beings infected with HTLV-III.

It has further been discovered that 3'-azido-3'-deoxythymidine (AZT), its 5'-mono-, 5'-di-, and 5'-triphosphates, and pharmaceutically acceptable salts thereof are active synergistically with interferon, in particular α-interferon, in treating human beings infected with HTLV-III. However, the synergistic action of AZT with β-interferon and with γ-interferon are also disclosed as features of this invention. When used in combination with interferon, in particular α-interferon, the suitable effective dose range of AZT is 5 to 250 mg per kg per day; and the suitable effective dose range of interferon is $3 \times 10^6$ IU per square meter of body surface per day, preferably $4 \times 10^6$ to $6 \times 10^6$ IU per square meter per day. The AZT and interferon should be administered in the ratio of from about 5 mg per kg of AZT to $3 \times 10^6$ IU per square meter of interferon to about 250 mg per kg per day of AZT to $10 \times 10^6$ IU per square meter per day of interferon, preferably from about 5 mg per kg per day of AZT to $4 \times 10^6$ IU per square meter per day of interferon to about 100 mg per kg per day of AZT to $6 \times 10^6$ IU per square meter per day of interferon.

Interferon is preferably administered by injection (s.c., i.m. or i.v., for example). AZT preferably administered orally or by injection, but may be administered by any mode described herein. Interferon and AZT may be administered together or separately, and the daily dose of each may preferably be administered as divided doses.

It has yet further been discovered that AZT, its 5'-mono-, 5'-di-, and 5'-triphosphates, and pharmaceutically acceptable salts thereof, are active synergistically with acyclovir, and pharmaceutically acceptable salts thereof, in treating human beings infected with HTLV-III. When used in combination with acyclovir, the suitable effective oral dose range of AZT is 2.5 to 50 mg per kg of body weight per day, preferably 5 to 10 mg per kg per day; and the suitable effective oral dose range of acyclovir is 5 to 100 mg per kg of body weight per day, preferably 15 to 75 mg per kg per day. It is preferred that the ratio for oral administration of AZT to acyclovir should be in the range of about 1:1 to 1:10, more preferably from about 1:2 to 1:8.

The suitable effective i.v. dose range of AZT is 1.5 to 15 mg per kg per day, and the suitable effective i.v. dose range of acyclovir is 5 to 30 mg per kg per day. It is preferred that the ratio for i.v. administration of AZT to acyclovir should be in the range of about 2:1 to 1:20, more preferably from about 1:2 to 1:10.

Both AZT and acyclovir are preferably administered orally or by injection and may be given together or separately. The daily dose of each may be given as divided doses.

Also disclosed is the use in combination with AZT of any of the compounds disclosed in U.S. Pat. No. 4,360,522, incorporated herein by reference, for the treatment of HTLV-III infections.

When AZT phosphates or pharmaceutically acceptable salts of AZT or its phosphates are used, the dose ranges and ratios of same with interferon or with acyclovir are calculated as AZT equivalent amounts. Likewise, when pharmaceutically acceptable salts of acyclovir are used, their amounts and ratios with AZT are calculated as acyclovir equivalent amounts.

We claim:

1. A method of treating a human being diagnosed as having Kaposi's sarcoma comprising administering to said human being a non-toxic, effective amount of 3'-azido-3'-deoxythymidine or its 5'-mono-, 5'-di-, or 5'-triphosphate, or a pharmaceutically acceptable salt thereof.

2. The method of claim 1 wherein 3'-azido-3'-deoxythymidine or a pharmaceutically acceptable salt thereof is administered.

3. The method of claim 1 wherein the 5'-monophosphate of 3'-azido-3'-deoxythymidine or a pharmaceutically acceptable salt thereof is administered.

* * * * *